United States Patent
Allegrini et al.

Patent Number: 5,543,533
Date of Patent: Aug. 6, 1996

[54] PHOTOCHROMIC PRODUCTS AND METHOD FOR THEIR PREPARATION

[75] Inventors: Pietro Allegrini, San Donato Milanese; Nereo Nodari, Mairago; Luciana Crisci, Graffignana; Vincenzo Malatesta, S. Maurilio, all of Italy

[73] Assignee: Great Lakes Chemical Italia S.r.l., Milan, Italy

[21] Appl. No.: 253,055

[22] Filed: Jun. 2, 1994

[30] Foreign Application Priority Data

Jun. 9, 1993 [IT] Italy ................... MI93A1215

[51] Int. Cl.$^6$ .......... C07D 311/92; C07D 409/00; C07D 265/00; C07D 405/00
[52] U.S. Cl. .......... 549/389; 544/71; 544/150; 544/375; 546/153; 546/155; 546/156; 546/196; 546/282.7; 548/409; 548/525; 524/99; 524/110; 252/586; 549/60
[58] Field of Search .................. 544/150, 375, 544/71; 546/153, 155, 156, 196, 269; 548/525, 409; 549/60, 389; 524/99, 110; 252/586

[56] References Cited

U.S. PATENT DOCUMENTS

| | | | |
|---|---|---|---|
| 4,818,096 | 4/1989 | Heller et al. | 544/70 |
| 5,238,981 | 8/1993 | Knowles | 524/110 |
| 5,244,602 | 9/1993 | Van Gemert | 549/60 |

FOREIGN PATENT DOCUMENTS

| | | |
|---|---|---|
| 0250193 | 12/1987 | European Pat. Off. |
| WO92/09593 | 6/1992 | WIPO |
| WO93/10112 | 5/1993 | WIPO |
| WO93/17071 | 9/1993 | WIPO |

*Primary Examiner*—Cecilia Tsang
*Attorney, Agent, or Firm*—Oblon, Spivak, McClelland, Maier & Neustadt, P.C.

[57] ABSTRACT

Photochromic products belonging to the group of chromenes having general formula (I):

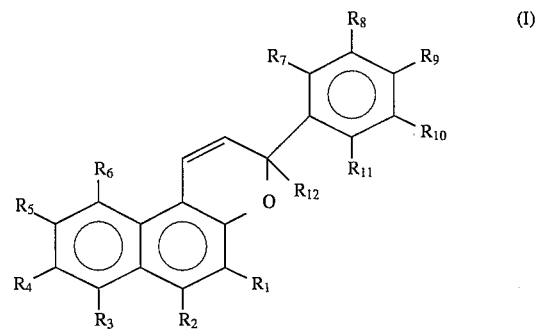

6 Claims, No Drawings

PHOTOCHROMIC PRODUCTS AND METHOD FOR THEIR PREPARATION

The present invention relates to new photochromic products.

More specifically the present invention relates to photochromic products belonging to the group of chromenes, a procedure for their preparation and their use in polymeric materials.

Photochromic products are substances which have the characteristic of reversibly changing colour and/or degree of light transmission when they are exposed to some types of electromagnetic radiation and solar light, returning to their original state of colour and light transmission when the initial source of light is removed.

There are numerous well-known substances having photochromic characteristics and belonging to different groups of both organic and inorganic products, as described, for example, in the texts "Photochromism" by G. H. Brown (Ed), Vol. III of the Weissberger series "Techniques of Organic Chemistry", Wiley Interscience, New York (1971) and in "Photochromism: Molecules and Systems", by H. Durr and H. Bouas-Laurent (Ed), Vol. 40 of the series "Studies in Organic Chemistry", Elsevier (1990).

Among organic photochromic products which are particularly well-known are those belonging to the group of spiro-indolino-oxazines, spiro-pyrans and chromenes. The above products are capable of giving photochromic characteristics to polymerized organic materials, used as photochromic articles, as described, for example, in patent applications: IT 22529 A/87, IT 22660 A/89, IT 19389 A/90, MI 91 A 002038 all filed by the Applicant, and in the following patents: U.S. Pat. Nos. 5,055,576, 5,110,922 both filed by the Applicant, U.S. Pat. Nos. 3,567,605, 5,066,818 and EP 245,020.

The photochromic products belonging to the above three groups can be suitably mixed to obtain, after irradiation with solar light or UV rays, the formation of a colouring as a result of the composition of colours of the products used. This composition of colours is particularly useful in the preparation of photochromic lenses composed of organic material for which neutral shades such as green, brown and grey are required by the market.

Photochromic products used in the field of lenses to obtain the colour blue or red are generally those belonging to the group of spiro-indolino-oxazines owing to their good colouring characteristics and fatigue resistance.

The colours yellow and orange are, on the other hand, generally obtained by using photochromic products belonging to the group of chromenes or spiro-pyrans as described, for example, in Italian patent MI 92 A 002379 and MI 92 A 002492 filed by the Applicant and in U.S. Pat. Nos. 5,066,818, 4,931,221 and EP 250,193.

In fact, although photochromic products of the group of spiro-indolino-oxazines which are capable of producing yellow or orange colouring are well-known, as described, for example, in U.S. Pat. No. 4,816,584, it is also known that these products are difficult to prepare owing to their low synthesis yield as described, for example, in "Photochromism" by G. H. Brown (Ed.), Vol. III of the Weissberger series "Techniques of Organic Chemistry", Wiley Interscience, New York (1971), page 244.

However also photochromic products belonging to the group of chromenes or spiro-pyrans have disadvantages. In fact, some photochromic products belonging to the group of chromenes have a photochromic activity only when the solution or end-product containing them are cooled to unacceptably low temperatures.

Moreover, some photochromic products belonging to the group of chromenes or spiro-pyrans have an aging-resistance which is too limited compared to other photochromic components of the above mixtures.

A further disadvantage arises from the low photochromic activity of products belonging to the group of chromenes or spiro-pyrans capable of developing a yellow colouring, owing to the effect of light absorption of a suitable wavelength. This disadvantage considerably limits the photochromic activity of mixtures of products suitable for developing neutral colouring such as green, brown and grey.

It is known, in fact, that the photochromic activity of products belonging to the groups of spiro-indolino-oxazines, chromenes and spiro-pyrans, cannot be arbitrarily increased by increasing the concentration of photochromic product. This is only possible when very low concentrations of active principle are used, whereas, over a certain concentration, an unsuperable limit value is reached.

On the basis of what is specified above, it is evident that neutral colouring must be obtained by limiting the concentration of additives which develop blue and red colouring, in-order to restrict their photochromic effect thus making them comparable to that of the yellow component.

The Applicant has now found photochromic products belonging to the group of chromenes capable of developing yellow and/or orange colouring, having a better photochromic activity with respect to those of the known art and capable of overcoming the above disadvantages.

The present invention therefore relates to photochromic products belonging to the group of chromenes having general formula (I):

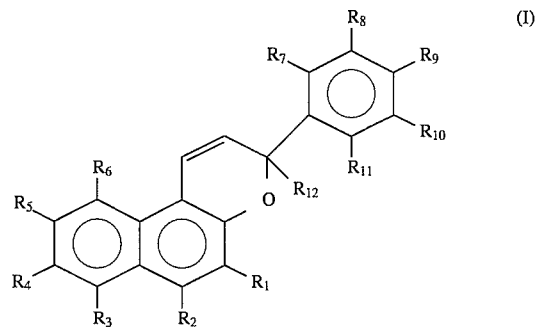

wherein:
a) the substituents from $R_1$ to $R_{11}$ each independently represent a hydrogen atom; a linear or branched $C_1$–$C_5$ alkyl group, possibly substituted with 1–5 halogen atoms selected from fluorine, chlorine bromine and iodine, hydroxy groups, $C_1$–$C_5$ alkoxy groups, $C_1$–$C_5$ acyloxy groups, $C_1$–$C_5$ alkyl carboxy groups, cyano groups; a $C_2$–$C_5$ alkenyl group; a benzyl group; a halogen atom selected from fluorine, chlorine, bromine and iodine; a hydroxy group; a $C_1$–$C_5$ alkoxy group; an amino group; a monoalkyl ($C_1$–$C_5$) amino group; a di-alkyl ($C_1$–$C_5$) amino group; a cyclo-alkyl ($C_3$–$C_{10}$) amino group; a piperidino, piperazino or morpholino group; a carboxyl group; a $C_1$–$C_5$ carboxyalkyl group; a $C_2$–$C_5$ carboxyalkenyl group; an amido carboxy group; a substituted N-alkyl ($C_1$–$C_5$) amido carboxy group; a substituted N,N-dialkyl ($C_1$–$C_5$) amido carboxy group; a cyano group; a nitro group; a sulphonic group; an alkyl ($C_1$–$C_5$) sulphonate group; an aryl sulphonate group; an aryl group selected from phenyl, biphenyl, naphthyl groups; an acyl group of the ketonic alkyl, ketonic aryl or ketonic benzyl type;

b) $R_{12}$ represents:
   an aromatic or heterocyclic group which can be represented by the following formulae (II), (III), (IV), (V), (VI), (VII) and (VIII):

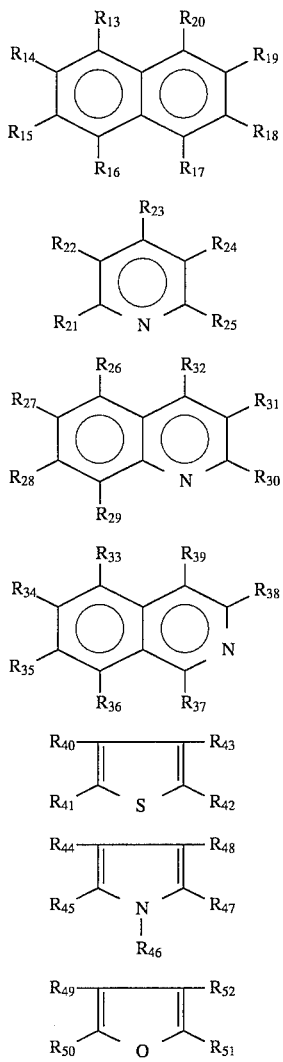

wherein:

$R_{46}$ represents a hydrogen atom; a $C_1$–$C_5$ alkyl group, linear or branched, possibly substituted with 1–5 halogen atoms selected from fluorine, chlorine, bromine and iodine, hydroxy groups, $C_1$–$C_5$ alkoxy groups, $C_1$–$C_5$ acyloxy groups, $C_1$–$C_5$ alkyl carboxy groups, cyano groups; a $C_2$–$C_5$ alkenyl group; a benzyl group; an aryl group selected from phenyl, biphenyl, naphthyl groups;

at least one of the substituents from $R_{13}$ to $R_{20}$, from $R_{21}$ to $R_{25}$, from $R_{26}$ to $R_{32}$, from $R_{33}$ to $R_{39}$, from $R_{40}$ to $R_{43}$, from $R_{44}$ to $R_{45}$ or from $R_{47}$ to $R_{48}$ and from $R_{49}$ to $R_{52}$, represent the link position with the pyranic ring the other substituents having the definition described under point (a).

Preferred products having general formula (I) according to the present invention are those wherein:

the substituents from $R_1$ to $R_{11}$, the same or different, each independently represent a hydrogen atom, a fluorine, chlorine, bromine atom, a methyl group, isopropyl group, trifluoromethyl group, hydroxymethyl group, benzyl group, hydroxy group, methoxy group, amino group, piperidino group, morpholino group, carboxyl group, carboxymethyl group, N,N-dimethylcarboxyamide group, cyano group, nitro group or phenyl group;

$R_{12}$ represents:

an aromatic or heterocyclic group which can be represented by formulae (II), (III) and (VI) wherein:

at least one of the substituents from $R_{13}$ to $R_{20}$, from $R_{21}$ to $R_{25}$, from $R_{40}$ to $R_{43}$, represents the link position with the pyran ring and the remaining substituents each independently represent a hydrogen atom, a fluorine, chlorine or bromine atom, a methyl group, isopropyl group, trifluoromethyl group, hydroxymethyl group, benzyl group, hydroxy group, methoxy group, amino group, piperidino group, morpholino group, carboxyl group, carboxymethyl group, N,N-dimethylcarboxyamide group, cyano group, nitro group, phenyl group, acetyl or benzoyl group.

Specific examples of preferred products according to the present invention are: 3-phenyl-3-(5-bromo-6-methoxy-2-naphthyl)-3H-naphtho-[2, 1b]-pyran (Ia):

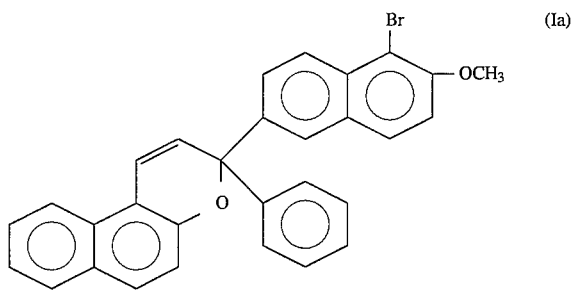

3-phenyl-3-(2-thienyl)-3H-naphtho-[2, 1b]-pyran (Ib):

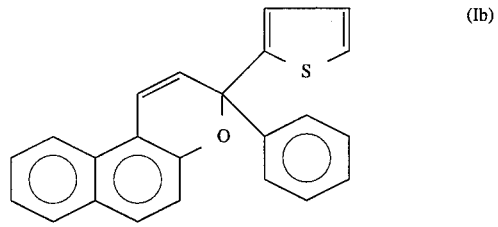

The present invention also relates to a procedure for the preparation of products having general formula (I).

The products having general formula (I) can be prepared by the reduction of the carbonyl group, followed by dehydration, of products having general formula (IX):

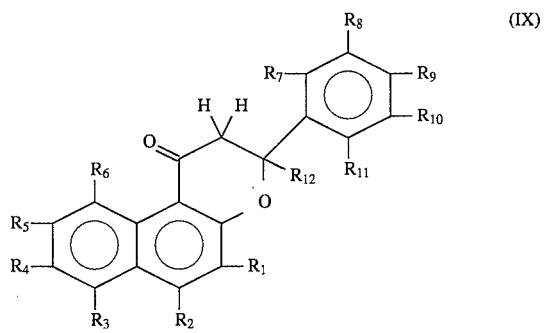

wherein the substituents from $R_1$ to $R_{12}$ have the same meaning described above.

The reduction reaction of the compound containing carbonyl group having general formula (IX) can be carried out using the conventional techniques such as catalytic hydrogenation, or using metal hydrides or products belonging to the group of boranes as described, for example, in the text "Chimica Organica Applicata" by U. Valcavi, ed. CLUED, Milano (1983).

The reduction reaction is generally carried out in the presence of metal hydrides such as, for example, the hydrides of aluminium and boron such as: LiAlH$_4$ (lithium aluminium hydride), AlH$_3$ (aluminium hydride), NaAlH$_4$ (sodium aluminium hydride), iBu$_2$AlH (diisobutyl aluminium hydride), LiAlH(tBuO)$_3$ (tri-terbutoxy lithium aluminium hydride), NaBH$_4$ (sodium boron hydride), (nC$_4$H$_9$)$_4$NBH$_4$ (tetrabutyl ammonium boron hydride), Ca(BH4)$_2$ (calcium boron hydride), LiBH$_4$ (lithium boron hydride), NaBH$_3$(CN) (sodium cyano boron hydride) and similar.

The metal hydrides described above are used in the presence of suitable inert solvents selected, depending on the hydride used, from aliphatic or aromatic hydrocarbons (such as pentane, hexane, heptane, benzene, toluene and xylene); chlorinated aliphatic or aromatic hydrocarbons (such as dichloromethane, 1,2-dichloroethane and chlorobenzene); aliphatic or aro-matic ethers (such as diethylene glycol dimethyl ether, diethyl ether, tetrahydrofuran and diphenylether); alcohols (such as methanol, ethanol, isopropanol and n-butanol); amides (such as dimethylformamide); esters (such as methyl acetate, ethyl acetate, butyl acetate); carbonates (such as dimethylcarbonate); water; mixtures of two or more solvents among those indicated above.

The reduction reaction in the presence of metal hydrides can be carried out at a temperature of between 0° C. and 200° C., preferably between 0° C. and 150° C. and for times of between 1 minute and 200 hours, preferably between 30 minutes and 50 hours.

The metal hydrides can be used in the reduction reaction in a quantity of between 1 and 50 equivalents per mole of product to be reduced, preferably between 1 and 20.

The possible excess of reducing agent can be eliminated by adding water or water acidified by the presence of acids such as, for example, sulphuric acid, hydrochloric acid or others.

The alcohol obtained can be subsequently purified by chromatography and/or crystallization from suitable solvents such as, for example, pentane, hexane, heptane, toluene, xylene, ethyl ether, methanol, ethanol, isopropanol, n-butanol, t-butanol, tetrahydrofuran, acetone, methylethylketone, ethyl acetate, dimethyl carbonate, acetonitrile, water and relative mixtures of two or more of the above solvents.

In accordance with another method, the alcohol obtained can be subjected to dehydration reaction directly in the crude reaction product.

The dehydration can be carried out by reacting the alcohol obtained as a pure product, or directly in the crude reaction product, with acids such as, for example, hydrochloric acid either gaseous or in an aqueous solution, hydrobromic acid, sulphuric acid, nitric acid, phosphoric acid, acetic acid, trifluoroacetic acid, methansulphonic acid, p-toluen sulphonic acid and others.

According to a preferred procedure, the dehydration reaction is carried out by heating the acid mixture resulting from the elimination of the excess reducing agent to a temperature of between 0° C. and 200° C., preferably between 20° C. and 150° C. and for times of between 1 minute and 24 hours, preferably between 5 minutes and two hours.

The water formed during the above dehydration reaction can be possibly eliminated azeotropically by means of a Dean-Stark apparatus.

The products having general formula (I) of the present invention can be recovered from the organic solution which contains them using the known techniques such as, for example, evaporation of the solvent under vacuum and subsequent purification of the crude product obtained by chromatography and/or crystallization.

The crystallization is carried out in the presence of suitable inert solvents selected from aliphatic or aromatic hyrdocarbons (such as pentane, hexane, heptane, benzene, toluene, xylene); aliphatic or aromatic ethers (such as ethyl ether, tetrahydrofuran, diphenylether); alcohols (such as methanol, ethanol, isopropanol, n-butanol, t-butanol); ketones (such as acetone, methylethylketone); esters (such as ethyl acetate); carbonates (such as dimethyl carbonate); nitriles (such as acetonitrile); organic acids (such as acetic acid); mixtures of one or more of the solvents listed above, with water.

The products having general formula (IX) are prepared by the condensation of 2-hydroxy-1-acetonaphthones having general formula (X):

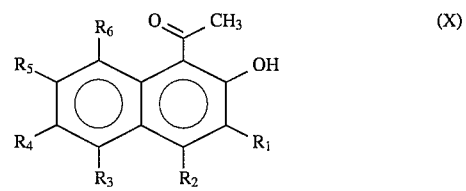

wherein the substituents from R$_1$ to R$_6$ have the meaning described above, with ketonic products having general formula (XI):

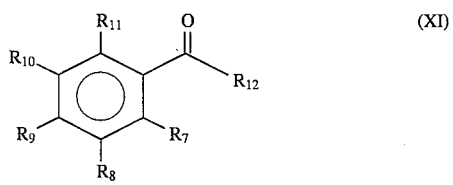

wherein the substituents from R$_7$ to R$_{12}$ have the meaning described above.

The condensation reaction is carried out operating according to the conditions described in literature such as, for example, in "Advanced Organic Chemistry" by J. March, IIIth edition, ed. Wiley Interscience (1985), pages 829–834 or, more specifically, in "Journal of the Chemical Society", by J. Cottam et al., page 5261 (1965).

The condensation reaction is carried out in the presence of products of the acid or, preferably basic type. Basic products which can be used for the purpose are, for example, alcoholates of alkaline metals (such as sodium or potassium methylate, ethylate, isopropylate, tert-butylate and others); amides (such as sodium amide, lithium amide, lithium diisopropylamide, N-lithium-( 2,2,6,6-tetramethyl)piperidine and others), lithium alkyls (such as ter-butyl lithium); hydrides of alkaline or alkaline-earth metals (such as lithium hydride, sodium hydride, potassium hydride, calcium hydride and others).

The basic products can be used in catalytic or stoichiometric quantities or even in great excess with respect to the 2-hydroxy-1-acetonaphthone having general formula (X).

When the basic-type product is used in a catalytic or stoichiometric quantity, it is necessary to previously carry out the salification of the phenolic function present in the 2-hydroxy-1-acetonaphthone having general formula (X) with a suitable base.

The salification reaction can be carried out in the presence of the same basic-type products used in the condensation reaction.

On the basis of what is specified above, the basic-type product can be used in a quantity of between 0.05 moles and 12 moles per mole of 2-hydroxy-1-acetonaphthone having general formula (X), preferably between 1.1 moles and 5 moles per mole of 2-hydroxy-1-acetonaphthone having general formula (X).

The molar ratio between the 2-hydroxy-1-acetonaphthone having general formula (X) and the ketonic product having general formula (XI) in the condensation reaction is between 0.1 and 6, preferably between 0.5 and 2.

The condensation reaction can be carried out in the presence of suitable solvents selected, depending on the basic-type product used, from aliphatic or aromatic hydrocarbons (such as pentane, hexane, heptane, benzene, toluene, xylene); chlorinated aliphatic or aromatic hydrocarbons (such as dichloromethane, 1,1-dichloroethane, chlorobenzene); aliphatic or aromatic ethers (such as diethylen glycol dimethyl ether, diethyl ether, tetrahydrofuran, diphenylether); alcohols (such as methanol, ethanol, isopropanol, n-butanol, t-butanol); amides (such as dimethylformamide); dimethylsulphoxide; mixtures of two or more of the above solvents.

The condensation reaction can be carried out at a temperature of between −78° C. and 200° C., preferably between 0° C. and 160° C. and for times of between 1 minute and 60 hours, preferably between 30 minutes and 30 hours.

At the end of the condensation reaction, the products having general formula (IX) can be obtained-by treatment of the reaction mass with acids such as, for example, hydrochloric acid, hydrobromic acid, sulphuric acid, phosphoric acid, acetic acid or their mixtures.

The products having general formula (IX) can be recovered from the organic solution containing them using the conventional techniques, such as, for example, evaporation of the solvent under vacuum and subsequent purification of the crude product obtained by chromatography and/or crystallization.

The crystallization is carried out in the presence of suitable inert solvents selected from aliphatic or aromatic hydrocarbons (such as pentane, hexane, heptane, benzene, xylene); aliphatic or aromatic ethers (such as ethyl ether, tetrahydrofuran); alcohols (such as methanol, ethanol, isopropanol, n-butanol, t-butanol); ketones (such as acetone, methylethylketone); esters (such as ethyl acetate); carbonates (such as dimethyl carbonate); nitriles (such as acetonitrile); organic acids (such as acetic acid); mixtures of one or more solvents among those indicated above, with water.

According to a preferred embodiment, the products having general formula (IX) can be subjected to the reduction reaction, described above, directly in the reaction medium.

Alternatively the products having general formula (I) of the present invention can be prepared by a process based on Claisen's rearrangement as described, for example, in European patent EP 246.114.

The products having general formula (I) of the present invention are crystalline products which are colourless or slightly yellow, yellow-orange or red-coloured.

Their solutions in common organic solvents (benzene, toluene, methanol) when not exposed to light sources, are colourless or slightly yellow.

These solutions, if exposed to a light source, both visible and ultraviolet, take on an intense yellow, yellow-orange or reddish colouring.

The colouring rapidly diminishes when the light source is removed.

The products having general formula (I) can be applied on the surface or incorporated in bulk in the desired articles, using the conventional techniques described hereunder.

Some polymeric photochromic products can be obtained with moulding techniques (for example injection or compression moulding) starting from polymers in which the product having general formula (I) is homogeneously dispersed in bulk.

Alternatively the product having general formula (I) can be dissolved in a solvent, together with the polymeric material such as, for example, polymethyl methacrylate, polyvinyl alcohol, polyvinyl butyral, acetate butyrate of cellulose or epoxy, polysiloxanic, urethanic resin. The mixture thus obtained is deposited on a transparent support to form, after evaporation of the solvent, a photochromic coating.

The product having general formula (I) can also be added to a polymerizable monomer such as, for example, a meth(acrylic) or allyl carbonate monomer, in such a way that, after polymerization carried out in the presence of a suitable initiator, such as azo-bis(isobutyronitrile) in the case of a meth(acrylic) monomer or peroxyketal in the case of an allyl carbonate monomer, they are uniformly incorporated in the resin formed.

Finally the product having general formula (I) can be applied to a transparent substrate such as, for example, polycarbonate, polymethyl methacrylate or polydiethylene glycol bis(allyl carbonate), by surface impregnation obtained by putting the substrate in contact, at a suitable temperature, with a solution or dispersion containing the product having general formula (I) according to the method described, for example, in U.S. Pat. No. 5,130,353.

The products having general formula (I) of the present invention have the characteristic of being able to be incorporated, in bulk or using one of the techniques described above, into polymers such as high density polyethylene, low density polyethylene, ethylene-vinylacetate copolymer, polyether amides, polypropylene, polymethylmethacrylate, polyvinyl alcohol, polyvinyl butyral, acetate butyrate of cellulose, epoxy, polysiloxanic or urethanic resins, polycarbonate, polydiethylen glycol bis(allyl carbonate), polyamides, polyesters.

The products having general formula (I) of the present invention have a photochromic acitivity even at room temperature and their photochromic activity is surprisingly higher than that of similar products belonging to the same group.

The products having general formula (I) of the present invention can be used in a mixture or combined with suitable organic photochromic products to obtain, after activation, the formation of neutral colouring such as green, brown and grey. Particularly useful for the purpose are photochromic products belonging to the group of spiro-indolino-oxazines and spiro-indolinopyrans described in the known art as, for example, in U.S. Pat. No. 5,066,818.

The experimental examples which follow are illustrative but do not limit the present invention in any way.

EXAMPLE 1

Preparation of 5-bromo-6-methoxy-2-naphthyl-phenylketone.

A solution of 1-bromo-2-methoxy-naphthalene (150 g; 0.63 moles) in methylene chloride (300 ml) are added dropwise over an hour to a solution of benzoyl chloride (74 ml; 0.64 mmoles) and anhydrous aluminium chloride (98.5 g; 0.74 moles) in methylene chloride (400 ml) cooled to 0° C. The addition is regulated in such a way that the temperature never exceeds 5° C.

When the addition dropwise has been completed, the reaction mixture is brought back to room temperature and kept so for 90 minutes. The mixture is subsequently poured into a cold solution of hydrochloric acid at 5%.

500 ml of methylene chloride are then added and the insoluble residue is eliminated by filtration. When the two phases obtained have been separated, the organic phase is washed with water (400 ml), with an aqueous solution of sodium bicarbonate at 10% (400 ml) and finally again with water (400 ml). The resulting organic phase is anhydrified on sodium sulphate and then dried.

The residue is crystallized from acetone (700 ml) thus obtaining 44 g (0.129 moles) of the desired product in the form of a white powder having an uncorrected melting point equal to 196° C.–199° C.

The product obtained has the following structural formula:

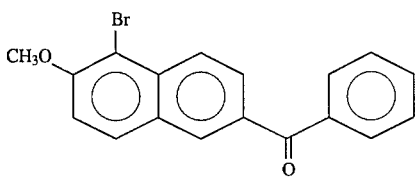

EXAMPLE 2

Preparation of 3-phenyl-3-(5-bromo-6-methoxy-2-naphthyl)-3H-naphtho-[2, 1b] -pyrano (Ia).

A hot solution of 2-hydroxy-1-acetonaphthone (3.5 g; 18.8 mmoles) and 5-bromo-6-methoxy-2-naphthyl-phenyl-ketone (7.7 g; 22.6 mmoles) in toluene (100 ml) are added dropwise in 30 minutes to a suspension of sodium amide (1.8 g; 46.2 mmoles) in toluene (30 ml) maintained at 60° C. under nitrogen and under mechanical stirring.

The temperature of the reagent mass is brought to 80° C. during the addition and subsequently maintained at this temperature for a further 4 hours.

The reaction mass, having a dark red colour, is poured into a mixture composed of 90 g of ground ice and 25 ml of concentrated hydrochloric acid.

After observing the colour change from dark red to yellow, 200 ml of toluene are added and the resulting suspension is heated to 40° C. before carrying out the separation of the two phases.

When the two phases have been separated, the organic phase is washed under heat with 100 ml of water before being added dropwise to a suspension of sodium boron hydride (1 g; 26.4 mmoles) in ethanol (35 ml).

The resulting mixture is kept under stirring for one night. 40 ml of hydrochloric acid at 10% are then added, the mass is heated to 40° C. for 90 minutes and 100 ml of water are then added and the two phases separated.

The organic phase is washed with 100 ml of water anhydrified on sodium sulphate and dried. The residue is subjected to chromatography on silica gel using toluene as eluant.

The fractions containing the product are concentrated to a total of 30 g and the product is left to crystallize for a night at room temperature.

The precipitate formed is filtered, washed with acetone and dried in the air.

3.75 g (7.6 mmoles) of product (Ia) are obtained, having the following characteristics:

m.p. (DSC): 171.7 ° C.

$^1$H-NMR (200 MHz, CDCl$_3$-TMS) δ (ppm): 3.98 (3H, s, CH$_3$O); 6.31 (1H, d); 7.19–7.53 (10H, m); 7.59–7.78 (4H, m); 7.91–7.99 (2H, m); 8.15 (H, d).

Mass spectrometry (DEP) (m/e): [M$^{.+}$ ion]: 492.

EXAMPLE 3

Preparation of 3-phenyl-3-(2-thienyl)-3H-naphtho-[2, 1b ] -pyrano (Ib).

A solution of 2-hydroxy-1-acetonaphthone (5 g; 26.9 mmoles) and p-methoxy-benzoyl-2-thiophene (6.46 g; 29.6 mmoles) in xylene (100 ml) are added, in 15 minutes, to a suspension of sodium amide (2.26 g; 57.9 mmoles) in xylene (80 ml) maintained at 85° C.

The charging funnel is washed with 20 ml of xylene. The resulting mixture is heated to 100° C., kept at this temperature for 3 hours and then heated to 125° C. and kept at this temperature for 26 hours.

The reaction mass is poured into a mixture composed of 100 g of ground ice and 30 ml of hydrochloric acid at 10%.

The suspension thus obtained is left under stirring for 30 minutes before adding 200 ml of toluene and carrying out the separation of the two phases. The organic phase is washed with two 100 ml portions of water before being added dropwise to a suspension of sodium boron hydride (1 g; 26.4 mmoles) in ethanol (40 ml).

The resulting mixture is kept under stirring at room temperature for one hour. 35 ml of hydrochloric acid at 10% are then added, the mass is heated to 40° C. for 45 minutes, 200 ml of water are subsequently added and the two phases separated.

The organic phase is washed with two 100 ml portions of water, anhydrified on sodium sulphate and dried. The residue is subjected to chromatography on silica gel, using a mixture of hexane:toluene in a ratio of 1:1, as eluant.

The solvent is removed from the fractions containing the product by Rotavapor and the dry residue is again subjected to chromatography on silica gel using, as eluant, a mixture of hexane:toluene 12:1. The fractions containing the product are then dried and the residue obtained is suspended in methanol and subsequently filtered.

After washing with methanol and drying in the air compound (Ib) is obtained, having the following characteristics:

m.p. (DSC): 120° C.

$^1$H-NMR (200 MHz, CDCl$_3$-TMS) δ (ppm): 3.77 (3H, s, CH$_3$O); 6.25 (1H, d); 6.8–6.96 (4H, m); 7.18 (1H, d); 7.23–7.38 (3H, m) ; 7.4–7.54 (3H; M); 7.59–7.78 (2H, m); 7.95 (1H, d).

Mass Spectrometry (DEP) (m/e): [ion M$^{.+}$]: 370

EXAMPLE 4

Evaluation of the Photochromic Activity of Compounds (Ia) and (Ib).

The photochromic activity was evaluated in toluene of products (Ia) and (Ib) obtained using the procedure described in examples 1 and 2, compared to that of the product having formula (R):

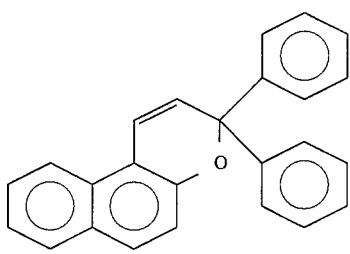
(R)

prepared according to the procedure described in "Journal of the Chemical Society" by J. Cottam et al., page 5261, (1965).

A $10^{-3}$M solution is prepared of the various products in toluene and charged into a quartz 1 mm cuvette.

The cuvette containing the solution is subjected to radiation with a Philips UVA lamp with an irradiance of 9 Watt/cm$^2$ placed at a fixed distance of 1 cm for 30 seconds.

The spectrum of the solution is registered before and after the radiation between 400 nm and 700 nm with a Hewlett Packard HP8452A spectrophotometer with photodiodes.

The difference between the luminous transmittance (Y) of the solution before and after radiation ($\Delta$Y) represents the photochromic activity of the product at the concentrations indicated.

Table 1 shows the values obtained.

TABLE 1

| PRODUCT | CONCENTRATION ($\times 10^{-3}$M) | $\Delta$Y | *$\lambda_{max}$ (nm) |
|---|---|---|---|
| (Ia) | 1.09 | 13.7 | 460 |
| (Ib) | 1.05 | 12.68 | 472 |
| (R) | 1.05 | 6.03 | 430 |

*$\lambda_{max}$: wavelength corresponding to the maximum absorption in the visible region of the activated form.

As can be seen from Table 1, the products of the present invention have a greater $\Delta$Y with respect to the $\Delta$Y of the product of the known art and therefore have a greater photochromic activity.

EXAMPLE 5

Preparation of Photochromic Lenses in Bulk.

Photochromic lenses are prepared according to the procedure described in patent application MI 92 A 002492 filed by the Applicant.

The allyl carbonate used is obtained by the reaction of diallyl carbonate (DAC) with a mixture of neopentyl glycol (NPG) and tris(hydroxyethyl) isocyanurate (THEIC) in the following proportions: NPG 70% by weight; THEIC 30% by weight; molar ratio DAC/(NPG+THEIC)= 5/1.

The product thus obtained is a complex mixture containing:
 bis(allyl carbonate) of neopentyl glycol, monomer and oligomers;
 tris(allyl carbonate) of tris(hydroxyethyl) isocyanide, monomer and oligomers;
 mixed allyl carbonates of neopentyl glycol and tris(hydroxyethyl) isocyanide.

The above product has the following physicochemical characteristics:
 Viscosity, 25° C. (cst): 80.
 Density, 20° C. (g/ml): 1.1411.
 $n_D^{20}$: 1.4595.

The polymerizable liquid compositions are prepared by mixing and homogenizing allyl carbonate (98.4%), perketal 1,1-di(ter-butylperoxy)-3,3,5-trimethylcyclohexane (1.5%) and photochromic compound R or (Ia) described in examples 4 and 2 respectively (0.1%).

The compositions thus obtained are transformed by polymerization into lenses having a thickness of 2 mm, using the conventional technique of casting. According to this technique the liquid composition containing the catalyst is poured into the cavity of a mould consisting of two glass elements, with a spacer gasket made of plasticized polyvinylchloride or copolymer ethylenevinyl acetate (EVA).

The liquid composition is polymerized in the mould by thermal treatment, in a forced-air oven, for 5 hours at 85° C., plus 15 hours at 90° C. and a further 7 hours at 100° C. At the end of this treatment, the moulds are opened, the polymerized products are recovered and the following characteristics are determined on the photochromic lenses thus obtained:

Photochromic properties, determined by recording the UV-visible spectra at 23° C. of the deactivated and activated forms, with a Hewlett Packard HP8452A spectrophotometer (activation for 60 seconds of radiation with a UVA lamp having a radiation of 9 W/m$^2$). The following values of deactivated and activated forms are registered:
 (a) O.D. ($\lambda_{max}$ UVA) and O.D. ($\lambda_{max}$ visible): values of optical density at $\lambda_{max}$ of absorption of the UVA and visible portions respectively;
 (b) Y: value of tristimulus colourimetry which indicates the value of luminous transmittance in the visible region, as defined in regulation CIE 1931. This value is obtained by mathematical processing of the absorption spectra of the two activated and deactived forms;
 (c) photochromic activity: expressed as $\Delta$Y which represents the difference between the luminous transmittance values.

Table 2 shows the data relating to the photochromic lenses obtained using photochromic product (Ia) compared to those relating to the photochromic lenses obtained using photochromic product R of the known art.

TABLE 2

| | Deactivated form | | | Activated form | | |
|---|---|---|---|---|---|---|
| Product | O.D. UVA ($\lambda_{max}$) | O.D. vis. ($\lambda_{max}$) | Y | O.D. vis. ($\lambda_{max}$) | Y | $\Delta$Y |
| (Ia) | 2.66 (340 nm) | 0.4566 (418 nm) | 90.36 | 0.7909 (418 nm) | 78.30 | 12.06 |
| R | 1.993 (360 nm) | 0.1898 (418 nm) | 95.21 | 0.8916 (418 nm) | 86.00 | 9.21 |

As can be seen from Table 2, the product of the present invention has a greater $\Delta$Y compared to the $\Delta$Y of the product of the known art and therefore has a greater photochromic activity.

We claim:

1. Photochromic products belonging to the group of chromenes, having the following formula (I):

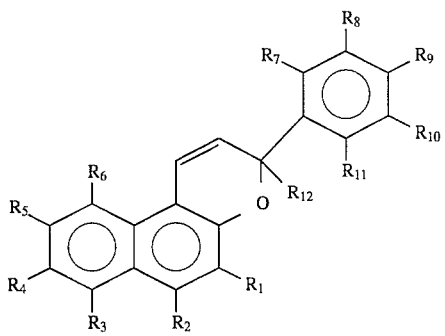

wherein in formula (I):

a) the substituents from $R_1$ to $R_6$ are each a hydrogen, and the substituents from $R_7$ to $R_{11}$ each independently represent a hydrogen atom; a linear or branched $C_1$–$C_5$ alkyl group, possibly substituted with 1–5 halogen atoms selected from fluorine, chlorine bromine and iodine, hydroxy groups, $C_1$–$C_5$ alkoxy groups, $C_1$–$C_5$ acyloxy groups, $C_1$–$C_5$ alkyl carboxy groups, cyano groups; a $C_2$–$C_5$ alkenyl group; a benzyl group; a halogen atom selected from fluorine, chlorine, bromine and iodine; a hydroxy group; a $C_1$–$C_5$ alkoxy group; an amino group; a monoalkyl ($C_1$–$C_5$) amino group; a di-alkyl ($C_1$–$C_5$) amino group; a cyclo-alkyl ($C_3$–$C_{10}$) amino group; a piperidino, piperazino or morpholino group; a carboxyl group; a $C_1$–$C_5$ carboxyalkyl group; a $C_2$–$C_5$ carboxyalkenyl group; an amido carboxy group; a N-alkyl ($C_1$–$C_5$) amido carboxy group; a N,N-dialkyl ($C_1$–$C_5$) amido carboxy group; a cyano group; a nitro group; a sulphonic group; an alkyl ($C_1$–$C_5$) sulphonate group; an aryl sulphonate group; an aryl group selected from phenyl, biphenyl, naphthyl groups; an acyl group of the ketonic alkyl, ketonic aryl or ketonic benzyl type;

b) $R_{12}$ represents:

an aromatic or heterocyclic group which can be represented by the following formulae (II), (III), (IV), (V), (VI), (VII) and (VIII):

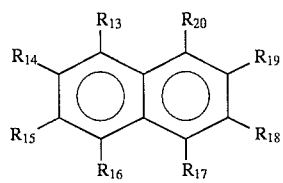

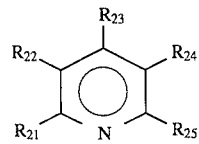

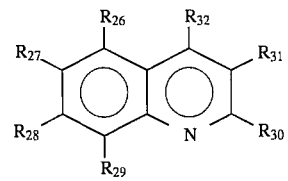

wherein:

$R_{46}$ represents a hydrogen atom; a $C_1$–$C_5$ alkyl group, linear or branched, possibly substituted with 1–5 halogen atoms selected from fluorine, chlorine, bromine and iodine, hydroxy groups, $C_1$–$C_5$ alkoxy groups, $C_1$–$C_5$ acyloxy groups, $C_1$–$C_5$ alkyl carboxy groups, cyano groups; a $C_2$–$C_5$ alkenyl group; a benzyl group; an aryl group selected from phenyl, biphenyl, naphthyl groups;

at least one of the substituents from $R_{13}$ to $R_{20}$ from $R_{21}$ to $R_{25}$, from $R_{26}$ to $R_{32}$, from $R_{33}$ to $R_{39}$ from $R_{40}$ to $R_{43}$, from $R_{44}$ to $R_{45}$ or from $R_{47}$ to $R_{48}$ and from $R_{49}$ to $R_{52}$, represent the link position with the pyran ring the other substituents having the definition described under point (a).

2. Photochromic compounds according to claim 1, wherein:

the substituents from $R_1$ to $R_6$ are each a hydrogen, and the substituents from $R_7$ to $R_{11}$, the same or different, each independently represent a hydrogen atom, a fluorine, chlorine, bromine atom, a methyl group, isopropyl group, trifluoromethyl group, hydroxymethyl group, benzyl group, hydroxy group, methoxy group, amino group, piperidino group, morpholino group, carboxyl group, carboxymethyl group, N,N-dimethylcarboxyamido group, cyano group, nitro group or phenyl group;

$R_{12}$ represents:

an aromatic or heterocyclic group which can be represented by formulae (II), (III) and (VI) wherein:

at least one of the substituents from $R_{13}$ to $R_{20}$, from $R_{21}$ to $R_{25}$, from $R_{40}$ to $R_{43}$, represents the link position with the pyran ring and the remaining substituents each independently represent a hydrogen atom, a fluorine, chlorine or bromine atom, a methyl group, isopropyl group, trifluoromethyl group, hydroxymethyl group, benzyl group, hydroxy group, methoxy group, amino group, piperidino group, morpholino group, carboxyl group, carboxymethyl group, N,N-dimethylcarboxyamido group, cyano group, nitro group, phenyl group, acetyl or benzoyl group.

3. Photochromic product according to claim 1 or 2, consisting of 3-phenyl-3-(5-bromo-6-methoxy-2-naphthyl)-3H-naphtho-[2,1b]-pyran (Ia).

4. Photochromic product according to claim 1 or 2, consisting of 3-phenyl-3-(2-thienyl)-3H-naphtho-[2, 1b]-pyrane (Ib).

5. Polymeric compositions consisting of at least one photochromic product having general formula (I) and at least one polymer selected from high density polyethylene, low density polyethylene, ethylene-vinylacetate copolymer, polyether amides, polypropylene, polymethylmethacrylate, polyvinyl alcohol, polyvinyl butyral, acetate butyrate of cellulose, epoxy, polysiloxanic or urethanic resins, polycarbonate, polydiethylen glycol bis(allyl carbonate), polyamides, polyesters.

6. Mixtures or combinations consisting of products having general formula (I) and organic photochromic products belonging to the group of spirooxazines and spiro-pyrans.

* * * * *